Aug. 28, 1956 P. DOT Plant Pat. 1,507
ROSE PLANT
Filed Oct. 26, 1955
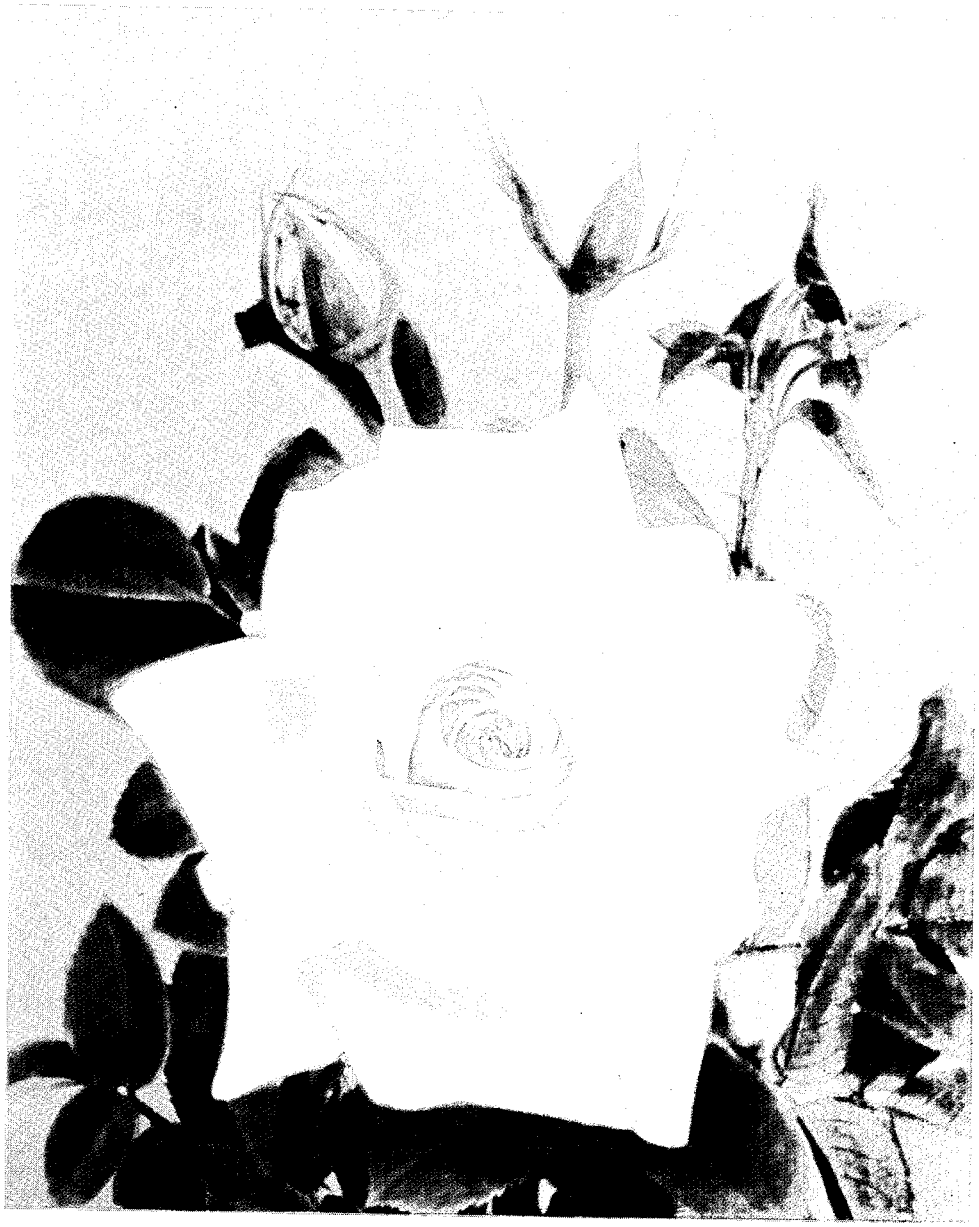
Inventor.
Pedro Dot
By: Robbins Robb
Attorneys.

United States Patent Office

Plant Pat. 1,507
Patented Aug. 28, 1956

1,507

ROSE PLANT

Pedro Dot, Barcelona, Spain, assignor to Cole Porter, New York, N. Y.

Application October 26, 1955, Serial No. 543,044

1 Claim. (Cl. 47—61)

The present invention relates to a new and distinct variety of rose plant of the hybrid tea class, which was originated by me by crossing the variety "Senateur Potie" (unpatented) with the variety "Poinsettia" (unpatented).

The primary objective in making this cross was to produce a new variety of rose embodying a combination of desirable qualities and characteristics that are not found together in any variety heretofore known in commerce. This objective was fully achieved, as evidenced by the fact that my new variety is particularly characterized by the following outstanding features:

(1) Its vigorous habit of growth;

(2) The excellent form of its buds and open blooms which is maintained from the bud stage through maturity;

(3) The great abundance of its flower petals;

(4) The firm texture of its flower petals, and their consequent resistance to adverse weather conditions;

(5) The clear pink general color tonality of its blooms which is maintained throughout the life thereof without significant fading or bluing; and (6) The unusually strong and clear fragrance of its flowers.

The foregoing chracteristics and distinctions definitely differentiate my new variety from its parents, as well as from all other varieties of its class of which I am aware, and asexual reproduction of my new variety by budding, as performed by me in Spain, and as performed at West Grove, Pennsylvania, U. S. A., shows that the unique combination of characteristics noted in the foregoing comes true to form and is established and transmitted through succeeding propagations.

The accompanying drawing shows typical specimens of the vegetative growth and flowers of my new variety in different stages of development and as depicted in color as nearly true as it is reasonably possibly to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—"Senateur Potie."

*Pollen parent.*—"Poinsettia."

Propagation: Holds its distinguishing characteristics through succeeding propagations by budding.

FLOWER

Locality where grown and observed: West Grove, Pennsylvania, U. S. A.

Flowers borne: Usually singly; on stems from medium length to long and of normal strength.

Quantity of bloom: Free, outdoors.

Continuity: Continuous.

Fragrance: Strong.

Bud:

*Peduncle.*—Medium length; medium caliper; erect; medium roughness; medium number of red hairs. Color—Oxblood Red, Plate 00823/3, with a greenish cast.

*Before calyx breaks.*—Size—medium. Form—Medium length; globular; with conspicuous neck; with foliaceous appendages on the surface of the bud; with slender, bristle-like foliaceous parts extending beyond the tip of the bud equal to ¾ of its length.

*As calyx breaks.*—Color—Spinel Pink, Plate 0625/2, varying to Spinel Pink, Plate 0625.

*As first petal opens.*—Size—medium. Form—Medium length; ovoid. Color: outside—Camellia Rose, Plate 622/1, shading to Apricot, Plate 609/2 suffused with pink and veined with Camellia Rose, Plate 622; inside—Camellia Rose, Plate 622/2, shading to Apricot, Plate 609/2, with a slight pink suffusion and veined with Camellia Rose, Plate 622.

*Opening.*—Opens up well.

Bloom:

*Size (when fully open).*—Large; from 4½ inches to 6 inches.

*Petalage.*—Very double; from 46 to 58 petals; arranged regularly.

*Form.*—Very full at first, but becoming globular; petals being loosely rolled outward from beginning to maturity.

Petals:

*Texture.*—Thick; leathery; with both inside and outside satiny.

*Shape.*—Outer petals—obovate; with 1 or 2 notches. Intermediate petals—obovate; usually with 1 notch, but sometimes with no notches. Inner petals—obovate; irregular; with an indefinite number of notches.

This description of a newly opened flower was made from a rose grown outdoors in the month of June, at West Grove, Pennsylvania, U. S. A:

*Color.*—Outer petal: outside surface—Rose Pink, Plate 427, shading abruptly to Apricot, Plate 609/1 lightly suffused with pink; inside surface—Rose Madder, Plate 23/3, thinly veined with China Rose, Plate 024 covering upper half of petal, and shading to Tangerine Orange, Plate 9/2 and Aureolin, Plate 3/1 at base of petal. Intermediate petal: outside surface—Rose Pink, Plate 427, shading to Tangerine Orange, Plate 9/2; inside surface—China Rose, Plate 024/2, shading to Mandarin Red, Plate 17/1, and then to Tangerine Orange, Plate 9/2 at base. Inner petal: outside surface—Carmine Rose, Plate 621/1, shading to Apricot, Plate 609/2 suffused with light pink; inside surface—Camellia Rose, Plate 622/1 at margin of petal, shading to Mandarin Red, Plate 17/1, with point of attachment Aureolin, Plate 3/1.

This description was made from a rose that was open for 3-days outdoors in the month of June, at West Grove, Pennsylvania, U. S. A.:

*Color.*—Outer petal: outside surface—Rose Madder, Plate 23/3, shading to Chinese Yellow, Plate 606/3 showing a slight pink suffusion; inside surface—Camellia Rose, Plate 622/2, shading to Camellia Rose, Plate 622/3, and then to Apricot, Plate 609/3, with point of attachment Aureolin, Plate 3/1. Inner petal: outside surface—Rose Madder, Plate 23/3, shading to Chinese Yellow, Plate 606/3 suffused with pink, and with point of attachment Sulphur Yellow, Plate 1/1; inside surface—Camellia Rose, Plate 622/1, shading to Apricot, Plate 609/2 showing pink suffusion, with point of attachment Sulphur Yellow, Plate 1/2.

*General color effect.*—Newly opened flower—China Rose, Plate 024/3, veined with China Rose, Plate 024; no orange coloration until petals are separated. 3-days open—from Camellia Rose, Plate 622/1 to Camellia Rose, Plate 622/2; orange coloration not visible until petals are separated.

*Behavior.*—Drop off cleanly.

*Flower longevity.*—On bush in garden—4 days in June. Cut flowers grown outdoors and kept at living-room temperatures—from 3 to 6 days in June.

REPRODUCTIVE ORGANS

Stamens: Medium number; arranged irregularly about pistils; mixed with petaloids; tucked in calyx.

Filaments: Many; most with anthers; medium length. Color—Apricot, Plate 609.

Anthers: All open at once; large; occasionally an anther fused with a petaloid. Color—Dresden Yellow, Plate 64/2.

Pollen: Moderate abundance. Color—Sulphur Yellow, Plate 1.

Pistils: Medium number.

Styles: Uneven; medium length; medium caliper; loosely bunched.

Stigma: Color—white.

Ovaries: Some protruding from calyx.

Hips: None.

Sepals: Permanent; moderately long; spear-shaped; recurved.

Seeds: None.

PLANT

Foliage:

*Leaves.*—Compound of 3 to many leaflets; normal abundance; medium size; leathery.

*Leaflets.*—Shape—generally oval, with apex mucronate. Base—acute. Margin—simply serrate.

*Color.*—Mature: upper surface—Parsley Green, Plate 00962/3; under surface—Willow Green, Plate 000862/1. Young: upper surface—Fern Green, Plate 0862/3, blotched and veined with Oxblood Red, Plate 00823/3; under surface—lighter tint of Oxblood Red, Plate 00823/3.

*Rachis (the supporting stem of the compound leaf).*—Medium caliper. Upper side—grooved and hairy; under side—moderately smooth.

*Stipules.*—Long; narrow; with moderately short points turning out at an angle of 45°.

*Disease resistance.*—Average resistance to mildew and blackspot, as compared with other varieties grown under the same cultural conditions at West Grove, Pennsylvania, U. S. A.

Growth:

*Habit.*—Bushy; upright; much-branched.

*Growth.*—From free to vigorous.

*Canes.*—Medium caliper.

*Main stems.*—Color—Lettuce Green, Plate 861. Thorns—many; medium length; hooked; pointed downward; with oval base of medium length. Prickles—few. Color—green. Hairs—none.

*Branches.*—Color—Oxblood Red, Plate 00823/1. Thorns—several; medium length; hooked; pointed downward; with narrow oval base of medium length. Prickles—few. Color—red. Hairs—none.

*New shoots.*—Color—Oxblood Red, Plate 00823/3. Thorns—several; medium length; hooked; pointed downward; with oval base of medium length. Prickles—none. Hairs—none.

I claim:

A new and distinct variety of rose plant of the hybrid tea class, substantially as herein shown and described, characterized particularly as to novelty by its vigorous habit of growth, the excellent form of its blooms and the retention of said form from bud to maturity, the great abundance of its flower petals, the firm texture of its flower petals and their consequent resistance to adverse weather conditions, the clear pink general color tonality of its blooms and the retention thereof without significant fading or bluing, and the unusually strong and clear fragrance of its blooms.

No references cited.